United States Patent
Holla

(10) Patent No.: US 6,908,752 B2
(45) Date of Patent: Jun. 21, 2005

(54) PROCESS FOR THE PREPARATION OF THE ENANT IOMERIC FORMS OF 2-SUBSTITUTED 2- (2, 5-DIOXOIMIDAZOLIDIN-1YL) -ACETIC ACID DERIVATIVES

(75) Inventor: Wolfgang Holla, Kelkheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 344 days.

(21) Appl. No.: 10/193,872

(22) Filed: Jul. 12, 2002

(65) Prior Publication Data

US 2003/0054507 A1 Mar. 20, 2003

(30) Foreign Application Priority Data

Jul. 14, 2001 (DE) .......................................... 101 34 366

(51) Int. Cl.[7] ............................ C12P 17/10; C12P 17/00
(52) U.S. Cl. ........................ 435/121; 435/117; 435/280
(58) Field of Search .................................. 435/121, 117

(56) References Cited

U.S. PATENT DOCUMENTS 4,588,694 A * 5/1986 Hamaguchi et al. ........ 435/280
6,331,552 B1  12/2001 Wehner et al.
6,399,643 B1  6/2002 Wehner et al.

FOREIGN PATENT DOCUMENTS

EP      0 149 674      7/1985
WO      WO 99/60015    11/1999

OTHER PUBLICATIONS

Haslam, Edwin, Recent Developments in Methods For The Esterification And Protection Of The Carboxyl Group, Tetrahedron, vol. 36., (1980), pp. 2409–2433.

Mammaghani, M, Enzymatic Kinetic Resolution of Aromatic Substituted Norbomene Mono–Esters Using Pig's Liver Esterase, Tetrahedron, vol. 58, (2002), pp. 147–151.

Roberti, Marinella, et al., Pig Liver Esterase (PLE)–Mediated Resolution of N–Substituted 4–Benzoyloxy–3–Carbomethoxypiperidines: A Convenient Preparation of 4–Hydroxy– And 4–Benzoyloxy–3–Carbomethoxypiperidines in Enantiomerically Pure Form, Tetrahedron, 11(2000), 4397–4405.

Salomon, Claudio, et al., Recent Developments In Chemical Deprotection of Ester Functional Groups, Tetrahedron, vol. 49, (1993), pp. 3691–3734.

Xiao, Xiao–yi, et al., Selective Solid Phase Synthesis of Ureas And Hydantoins From Common Phenyl Carbamate Intermediates, J. Org. Chem., 62, (1997), pp. 6968–6973.

* cited by examiner

Primary Examiner—Herbert J. Lilling
(74) Attorney, Agent, or Firm—George Wang

(57) ABSTRACT

The present invention relates to a process for the preparation of the enantiomeric forms of 2-substituted 2-(2,5-dioxoimidazolidin-1-yl)acetic acid derivatives of the formula I,

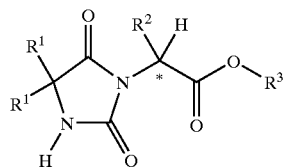

I wherein $R^1$, $R^2$ and $R^3$ have the meanings given in the claims, by stereodifferentiating conversion of mixtures of the enantiomers with the aid of enzymes.

8 Claims, No Drawings

PROCESS FOR THE PREPARATION OF THE ENANTIOMERIC FORMS OF 2-SUBSTITUTED 2- (2, 5-DIOXOIMIDAZOLIDIN-1YL) -ACETIC ACID DERIVATIVES

BACKGROUND OF THE INVENTION

The present invention relates to a process for the preparation of the enantiomeric forms of 2-substituted 2-(2,5-dioxoimidazolidin-1-yl)acetic acid derivatives of the formula I,

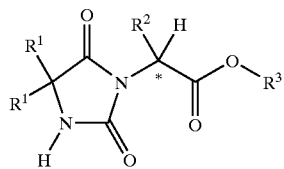

wherein $R^1$, $R^2$ and $R^3$ have the meanings given below, by stereodifferentiating conversion of mixtures of the enantiomers with the aid of enzymes.

The chiral acetic acid derivatives of the formula I, which carry a 2-(2,5-dioxoimidazolidin-1-yl) residue and a further substituent $R^2$ in the 2-position of the acetic acid unit, are key building blocks or precursors for a range of potent active pharmaceutical ingredients as described, for example, in EP-A-918059 and its counterparts including U.S. Pat. No. 6,331,552, or in WO-A-99/60015 or WO-A-00/69831 and its counterpart U.S. Pat. No. 6,399,643. All of the aforementioned references are incorporated herein by reference. The active ingredients described in these documents are inhibitors of the adhesion and migration of leukocytes and/or antagonists of the integrin adhesion receptor VLA-4 and are suitable, for example, for therapy and prophylaxis of inflammatory disorders, for example rheumatoid arthritis, of allergic disorders or of asthma or atherosclerosis. For preparing active pharmaceutical ingredients which are present in stereochemically homogenous form at the chiral carbon atom in the 2-position of 2-substituted 2-(2,5-dioxoimidazolidin-1-yl)acetic acid unit, stereochemically homogeneous building blocks are used as starting materials which may first have to be synthesized in a complex manner from stereochemically homogeneous starting materials, or mixtures of stereoisomeric compounds have to be separated in a laborious manner, for example by chromatography. For the production of active pharmaceutical ingredients of this type on an industrial scale in particular, there is therefore a need for a simple and cost-effective route to the enantiomeric forms of the compounds of the formula I in sufficient enantiomeric purity (optical purity). An optical resolution or enantiomer separation of the racemic compounds of the formula I, which are obtainable in a simple way, for example, from the racemic 2-substituted 2-aminoacetic acid derivatives by formation of the hydantoin ring or by alkylation of the hydantoin with racemic 2-substituted 2-haloacetic acid derivatives, is hitherto unknown.

Surprisingly, it was found that, although an enzymatic optical resolution of compounds of the formula I by stereoselective hydrolysis of compounds wherein $R^3$ has a meaning other than hydrogen does not succeed in a useful manner with a large number of enzymes, there nevertheless is a certain group of enzymes which provides the individual enantiomeric forms in pure form from mixtures of enantiomeric compounds of the formula I. Among the enzymes found to be unsuitable are, for example, lipases, in fact not only lipases of microbial origin and lipases from Candida spec. or Pseudomonas spec. but also lipases from the bovine or porcine pancreas. Just so proteases and peptidases such as subtilisin or pronase were found to be unsuitable for the enzymatic optical resolution of compounds of the formula I. Surprisingly, a sufficient conversion and a good stereoselectivity were only observed using esterases such as mammalian liver esterases or mammalian liver acetone powders, which allow the separation of enantiomeric mixtures of compounds of the formula I into their optically pure enantiomeric forms in a simple and efficient manner.

DESCRIPTION OF THE INVENTION

The present invention therefore provides a process for the preparation of a compound of the formula I,

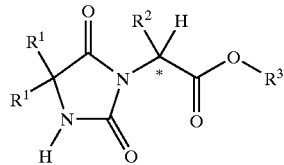

wherein the two $R^1$ residues are identical and are hydrogen, fluorine, $(C_1-C_4)$-alkyl, $(C_2-C_4)$-alkenyl, $(C_2-C_4)$-alkynyl or $(C_3-C_4)$-cycloalkyl, where alkyl, alkenyl, alkynyl and cycloalkyl can be substituted by 1, 2 or 3 identical or different substituents selected from the group consisting of fluorine, chlorine, bromine and methoxy, or the two $R^1$ residues together are tetramethylene —$(CH_2)_4$— or pentamethylene —$(CH_2)_5$—;

$R^2$ is fluorine, chlorine, bromine, nitro, cyano, hydroxyl, methoxy, acetylamino, tert-butyloxycarbonylamino, benzyloxycarbonylamino, methylmercapto, tert-butylmercapto, $(C_1-C_{10})$-alkyl, aryl, aryl-$(C_1-C_{10})$-alkyl-, heteroaryl, heteroaryl-$(C_1-C_{10})$-alkyl-, $(C_2-C_{10})$-alkenyl, $(C_2-C_{10})$-alkynyl, $(C_3-C_7)$-cycloalkyl or $(C_3-C_7)$-cycloalkyl-$(C_1-C_{10})$-alkyl-, where alkyl, aryl, heteroaryl, alkenyl, alkynyl and cycloalkyl can be substituted by 1, 2 or 3 identical or different substituents selected from the group consisting of fluorine, chlorine, bromine, iodine, trifluoromethyl, methyl, nitro, cyano, acetylamino, 9-fluoroenylmethyloxycarbonylamino, tert-butyloxycarbonylamino, benzyloxycarbonylamino, mercapto, methylmercapto, tert-butylmercapto, hydroxyl, methoxy, ethoxy and $COOR^4$;

$R^3$ is hydrogen, $(C_1-C_{10})$-alkyl, aryl-$(C_1-C_{10})$-alkyl-, $(C_2-C_{10})$-alkenyl, $(C_3-C_{10})$-alkynyl, $(C_3-C_7)$-cycloalkyl or $(C_3-C_7)$-cycloalkyl-$(C_1-C_{10})$-alkyl-, where alkyl, aryl, alkenyl, alkynyl and cycloalkyl can be substituted by 1, 2 or 3 identical or different substituents selected from the group consisting of fluorine, chlorine, bromine, iodine, trifluoromethyl, methyl, cyano, nitro, acetylamino, tert-butyloxycarbonylamino, benzyloxycarbonylamino, hydroxyl, methoxy, ethoxy and $COOR^5$;

$R^4$ and $R^5$, which can be identical or different, are hydrogen, $(C_1-C_4)$-alkyl, $(C_2-C_4)$-alkenyl or aryl-$(C_1-C_{10})$-alkyl-;

or a salt thereof, in substantially enantiomerically pure form, which comprises subjecting a mixture of the enantiomeric forms of a compound of the formula I wherein $R^3$ has a meaning other than hydrogen, to an enzymatic hydrolysis with the aid of an esterase and separating the converted and unconverted compounds from each other. The stereocenter at which the compound of the formula I after conducting the process of the invention is present in substantially enantiomerically pure form is marked by the asterisk * in the formula I.

Alkyl, alkenyl and alkynyl residues in the compounds of the formula I can be straight-chain or branched. This also applies when they are substituted or occur as substituents of other residues. Examples of alkyl residues include methyl, ethyl, n-propyl, n-butyl, n-pentyl, n-hexyl, n-heptyl, n-octyl, n-nonyl, n-decyl, isopropyl, isobutyl, isopentyl, isohexyl, 3-methylpentyl, neopentyl, neohexyl, 2,3,5-trimethylhexyl, sec-butyl, tert-butyl, tert-pentyl. Preferred alkyl residues are methyl, ethyl, n-propyl, isopropyl, n-butyl, isobutyl and tert-butyl. In one embodiment of the present invention, alkyl residues, or in general the residues $R^1$, $R^2$ and $R^3$, in the compounds of the formula I have no chiral center, so that in this embodiment, the chiral carbon atom to which the residue $R^2$ is bonded is the only chiral center in the compounds of the formula I. Examples of substituted alkyl residues include hydroxymethyl, 2-hydroxyethyl, 3-hydroxypropyl, 4-hydroxybutyl, 6-hydroxyhexyl, bromomethyl, 3-bromopropyl, chloromethyl, trichloromethyl, trifluoromethyl, 2,2,2-trifluoroethyl, methoxymethyl, 2-methoxyethyl, 3-methoxypropyl, cyanomethyl, 2-cyanoethyl, methylmercaptomethyl, 2-methylmercaptoethyl, tert-butylmercaptomethyl, 2-acetylaminoethyl, 3-benzyloxycarbonylaminopropyl, 3-tert-butoxycarbonylaminopropyl, hydroxycarbonylmethyl, 2-hydroxycarbonylethyl, 2-tert-butoxycarbonylethyl.

Alkenyl and alkynyl residues preferably contain a double bond or a triple bond which can be located at any position. Examples of alkenyl and alkynyl residues are vinyl, 1-propenyl, 2-propenyl(=allyl), 2-butenyl, 3-butenyl, 2-methyl-1-propenyl, 2-methyl-2-propenyl, 3-methyl-2-butenyl, 2-hexenyl, 5-hexenyl, 2-decenyl, ethynyl, 1-propynyl, 2-propynyl(=propargyl), 2-butynyl, 3-butynyl, 2-hexynyl, 4-hexynyl or 5-hexynyl.

Examples of cycloalkyl residues are cyclopropyl, cyclobutyl, cyclopentyl, cyclohexyl and cycloheptyl. Preferred cycloalkyl residues are on the one hand cyclopropyl and on the other hand cyclopentyl and cyclohexyl. Examples of substituted cycloalkyl residues are 3,4-dimethylcyclopentyl, 4-methylcyclohexyl, 3,3-dimethylcyclohexyl, 4,4-dimethylcyclohexyl, 4-tert-butyfcyclohexyl, 4-hydroxycyclohexyl. Examples of cycloalkyl-alkyl residues are cyclopropylmethyl, 2-cyclopropylethyl, 3cyclopropylpropyl, cyclobutylmethyl, cyclopentylmethyl, 2-cyclopentylethyl, cyclohexylmethyl, 2-cyclohexylethyl, 3-cyclohexylpropyl, cycloheptylmethyl, which can be substituted in the cycloalkyl moiety and/or in the alkyl moiety as previously stated.

Examples of aryl residues include phenyl, 1-naphthyl, 2-naphthyl, 2-biphenylyl, 3-biphenylyl, 4-biphenylyl or fluoroenyl. A preferred aryl group is phenyl. Examples of arylalkyl residues include benzyl, 1-phenylethyl, 2-phenylethyl, 3-phenylpropyl, 4-phenylbutyl, 2-, 3- and 4-biphenylylmethyl, (1-naphthyl)methyl, (2-naphthyl) methyl, 2-(1-naphthyl)ethyl, 2-(2-naphthyl)ethyl, 9-fluoroenylmethyl, which can be substituted in the aryl moiety and/or in the alkyl moiety as previously stated.

Heteroaryl is preferably a residue of a monocyclic or bicyclic aromatic ring system which contains one, two or three or four, preferably one or two, identical or different ring hetero atoms selected from the group consisting of nitrogen, oxygen and sulfur, and can be bonded through any suitable ring atom. Examples of heteroaryl residues include pyrrolyl, furanyl, for example 2-furanyl and 3-furanyl, thienyl, for example 2-thienyl and 3-thienyl, imidazolyl, for example 2-imidazolyl and 4-imidazolyl, pyrazolyl, 1,3-oxazolyl, 1,2-oxazolyl, 1,3-thiazol, for example 1,3-thiazol-2-yl and 1,3-thiazol-4-yl, 1,2-thiazolyl, tetrazolyl, pyridyl, for example 2-pyridyl, 3-pyridyl and 4-pyridyl, pyrazinyl, pyrimidinyl, indolyl, for example 2-indolyl, 3-indolyl and 5-indolyl, benzothienyl, benzofuranyl, quinolinyl, isoquinolinyl, quinoxalinyl, quinazolinyl.

Examples of heteroarylalkyl residues are 2-pyridylmethyl, 3-pyridylmethyl, 4-pyridylmethyl, 2-(2-pyridyl)ethyl, 2-(3-pyridyl)ethyl, 2-(4-pyridyl)ethyl, 2-furylmethyl, 3-furylmethyl, 2-thienylmethyl, 3-thienylmethyl, 4-imidazolylmethyl, 3-indolylmethyl, 2-(3-indolyl)ethyl, which can be substituted in the heteroaryl moiety and/or in the alkyl moiety as stated.

Substituted alkyl residues, alkenyl residues, alkynyl residues, cycloalkyl residues, aryl residues and heteroaryl residues can be substituted in any position, provided that the resulting molecule is sufficiently stable and has suitable properties for the intended use. In monosubstituted phenyl residues, the substituent can be located in the 2-position, the 3-position or 4-position. Disubstituted phenyl can be 2,3-substituted, 2,4-substituted, 2,5-substituted, 2,6-substituted, 3,4-substituted or 3,5-substituted. Trisubstituted phenyl residues can be 2,3,4-substituted, 2,3,5-substituted, 2,4,5-substituted, 2,4,6-substituted, 2,3,6-substituted or 3,4,5-substituted. Monosubstituted 1-naphthyl residues can be substituted in the 2-, 3-, 4-, 5-, 6-, 7- or 8-position, monosubstituted 2-naphthyl residues in the 1-, 3-, 4-, 5-, 6-, 7- or 8-position.

Examples of salts of compounds of the formula I include alkali metal salts, alkaline earth metal salts or ammonium salts of compounds which contain one or more hydroxycarbonyl groups, for example lithium, sodium, potassium, magnesium or calcium salts or salts which contain the unsubstituted ammonium ion or ammonium ions with one, two, three or four identical or different organic residues, for example methyl-, dimethyl-, triethyl-, tris(2-hydroxyethyl)- or 1,1,1-tris(hydroxymethyl)methyl-ammonium ions. In salts of the compounds of the formula I also two or more different cations can be present. Salts furthermore included are acid addition salts of compounds of the formula I which contain basic groups, for example nitrogen heterocycles, with inorganic acids or organic carboxylic acids or sulfonic acids, for example hydrochloric acid, sulfuric acid, phosphoric acid, acetic acid, tartaric acid or methanesulfonic acid. Compounds of the formula I which contain both acid groups and basic groups can also be present in the form of internal salts, zwitterions or betaines.

When the two $R^1$ residues together are tetramethylene or pentamethylene, the spiro compounds of the formula Ia or Ib are present.

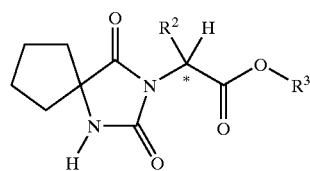

Ia

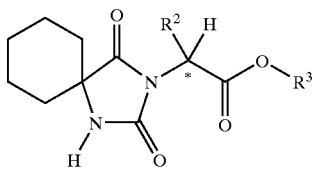

Ib

When the $R^1$ residues together are not a polymethylene chain, the two $R^1$ residues which are identical are preferably hydrogen, methyl, ethyl, propyl or trifluoromethyl, more preferably hydrogen, methyl or trifluoromethyl, most preferably methyl or trifluoromethyl, in particular methyl.

$R^2$ is preferably $C_1$–$C_6$)-alkyl, phenyl, phenyl-($C_1$–$C_4$)-alkyl-, such as benzyl, ($C_3$–$C_6$)-cycloalkyl or ($C_3$–$C_6$)-cycloalkyl-($C_1$–$C_4$)-alkyl-, where alkyl, cycloalkyl and phenyl can be substituted as stated. $R^2$ is more preferably ($C_1$–$C_6$)-alkyl or ($C_3$–$C_6$)-cycloalkyl-($C_1$–$C_4$)-alkyl-, most preferably ($C_1$–$C_6$)-alkyl or ($C_3$–$C_6$)-cycloalkyl-($C_1$–$C_2$)-alkyl-, especially preferably ($C_1$–$C_6$)-alkyl or cyclopropyl-($C_1$–$C_2$)-alkyl-, and even more preferably isobutyl (($CH_3$)$_2$CH—$CH_2$—) or cyclopropylmethyl (cyclopropyl-$CH_2$—).

In the compounds of the formula I which are employed in the enzymatic optical resolution and in which $R^3$ is not hydrogen, $R^3$ is preferably ($C_1$–$C_{10}$)-alkyl, which can be substituted as stated, more preferably ($C_1$–$C_6$)-alkyl, most preferably ($C_1$–$C_4$)-alkyl, especially preferably methyl or ethyl. In the compounds of the formula I which are obtained when the enzymatic optical resolution is carried out, $R^3$ can additionally be hydrogen in each of these preferred embodiments, i.e. the compounds of the formula I in which the group COOR$^3$ is the carboxylic acid group COOH or a salt thereof are also encompassed.

In one embodiment of the invention, the residues $R^4$ and $R^5$ are hydrogen or ($C_1$–$C_4$)-alkyl. In another embodiment of the invention, in the compounds of the formula I which are employed in the enzymatic optical resolution and in which $R^3$ has a meaning other than hydrogen, the $R^4$ and $R^5$ residues are hydrogen. When an alkyl, alkenyl, alkynyl, cycloalkyl, aryl or heteroaryl residue representing $R^2$ or $R^3$ is substituted, in a further embodiment of the invention this residue does not carry any COOR$^4$ or COOR$^5$ substituents. If desired, in preparing certain compounds of the formula I the meanings of $R^4$ and $R^5$ can be selected such that the reactivities of the groups COOR$^4$ and/or COOR$^5$ are different from the reactivity of the group COOR$^3$. The groups COOR$^4$ and/or COOR$^5$ can then be modified after carrying out the optical resolution of the invention.

In a preferred embodiment, the invention relates to a process for the preparation of a compound of formula I, wherein the two $R^1$ residues are identical and are hydrogen, methyl or trifluoromethyl, or the two $R^1$ residues together are tetramethylene —($CH_2$)$_4$— or pentamethylene —($CH_2$)$_5$—, and preferably the two $R^1$ residues are both methyl or trifluoromethyl;

$R^2$ is ($C_1$–$C_6$)-alkyl or ($C_3$–$C_6$)-cycloalkyl-($C_1$–$C_2$)-alkyl-, and is preferably isobutyl or cyclopropylmethyl;

$R^3$ is hydrogen or ($C_1$–$C_4$)-alkyl, and is preferably hydrogen, methyl or ethyl; or of a salt thereof, in substantially enantiomerically pure form, which comprises subjecting a mixture of the enantiomeric forms of a compound of the formula I wherein $R^3$ has a meaning other than hydrogen to an enzymatic hydrolysis with the aid of an esterase and separating the converted and unconverted compounds from each other.

The following compounds are examples of compounds of the formula I which can be employed in the enzymatic optical resolution, as mixtures of enantiomers, in the form of the corresponding methyl or ethyl esters, for example, and can be obtained in the form of the specified acids or in the form of the corresponding unreacted esters in substantially enantiomerically pure form:

(R)-2-(2,5-Dioxoimidazolidin-1-yl)-4-methylpentanoic acid
(S)-2-(2,5-Dioxoimidazolidin-1-yl)-4-methylpentanoic acid
(R)-2-(4,4-Dimethyl-2,5-dioxoimidazolidin-1-yl)-4-methylpentanoic acid
(S)-2-(4,4-Dimethyl-2,5-dioxoimidazolidin-1-yl)-4-methylpentanoic acid
(R)-2-(4,4-Bis(trifluoromethyl)-2,5-dioxoimidazolidin-1-yl)-4-methylpentanoic acid
(S)-2-(4,4-Bis(trifluoromethyl)-2,5-dioxoimidazolidin-1-yl)-4-methylpentanoic acid
(R)-2-(4,4-Tetramethylene-2,5-dioxoimidazolidin-1-yl)-4-methylpentanoic acid
(S)-2-(4,4-Tetramethylene-2,5-dioxoimidazolidin-1-yl)-4-methylpentanoic acid
(R)-2-(4,4-Pentamethylene-2,5-dioxoimidazolidin-1-yl)-4-methylpentanoic acid
(S)-2-(4,4-Pentamethylene-2,5-dioxoimidazolidin-1-yl)-4-methylpentanoic acid
(R)-2-(2,5-Dioxoimidazolidin-1-yl)-3-cyclopropylpropionic acid
(S)-2-(2,5-Dioxoimidazolidin-1-yl)-3-cyclopropylpropionic acid
(R)-2-(4,4-Dimethyl-2,5-dioxoimidazolidin-1-yl)-3-cyclopropylpropionic acid
(S)-2-(4,4-Dimethyl-2,5-dioxoimidazolidin-1-yl)-3-cyclopropylpropionic acid
(R)-2-(4,4-Bis(trifluoromethyl)-2,5-dioxoimidazolidin-1-yl)-3-cyclopropylpropionic acid
(S)-2-(4,4-Bis(trifluoromethyl)-2,5-dioxoimidazolidin-1-yl)-3-cyclopropylpropionic acid
(R)-2-(4,4-Tetramethylene-2,5-dioxoimidazolidin-1-yl)-3-cyclopropylpropionic acid
(S)-2-(4,4-Tetramethylene-2,5-dioxoimidazolidin-1-yl)-3-cyclopropylpropionic acid
(R)-2-(4,4-Pentamethylene-2,5-dioxoimidazolidin-1-yl)-3-cyclopropylpropionic acid
(S)-2-(4,4-Pentamethylene-2,5-dioxoimidazolidin-1-yl)-3-cyclopropylpropionic acid
(R)-2-(2,5-Dioxoimidazolidin-1-yl)-3-phenylpropionic acid
(S)-2-(2,5-Dioxoimidazolidin-1-yl)-3-phenylpropionic acid
(R)-2-(4,4-Dimethyl-2,5-dioxoimidazolidin-1-yl)-3-phenylpropionic acid
(S)-2-(4,4-Dimethyl-2,5-dioxoimidazolidin-1-yl)-3-phenylpropionic acid
(R)-2-(4,4-Bis(trifluoromethyl)-2,5-dioxoimidazolidin-1-yl)-3-phenylpropionic acid
(S)-2-(4,4-Bis(trifluoromethyl)-2,5-dioxoimidazolidin-1-yl)-3-phenylpropionic acid
(R)-2-(4,4-Tetramethylene-2,5-dioxoimidazolidin-1-yl)-3-phenylpropionic acid
(S)-2-(4,4-Tetramethylene-2,5-dioxoimidazolidin-1-yl)-3-phenylpropionic acid
(R)-2-(4,4-Pentamethylene-2,5-dioxoimidazolidin-1-yl)-3-phenylpropionic acid
(S)-2-(4,4-Pentamethylene-2,5-dioxoimidazolidin-1-yl)-3-phenylpropionic acid The enantiomeric forms of the compounds of the formula I obtained by carrying out the optical resolution of the invention, i.e. the R form and the S form, can be represented by the formulae Ic and Id,

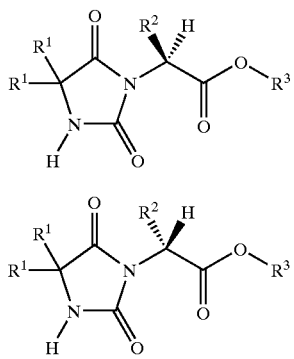

where the assignment of the stereochemical designations R and S to the formulae depends on the $R^2$ residue.

The preparation of the racemic starting compounds for the process of the invention, i.e. the compounds of the formula I wherein $R^3$ has a meaning other than hydrogen, can, for example, take place starting from racemic 2-substituted haloacetic acid derivatives or amino acid derivatives or dipeptides according to the processes in EP-A-918059 and its counterparts including U.S. Pat. No. 6,331,552 or in X. Xiao et al., J. Org. Chem. 1997, 62, 6968, and the literature cited therein. However, besides racemic mixtures just so non-racemic mixtures can be used in the process of the invention, i.e. mixtures which contain the two enantiomeric forms in a ratio other than 1:1. In the context of the present invention starting mixtures of this kind are always encompassed as well when, for example, the enzymatic resolution of a racemic mixture is discussed.

The process of the invention for enzymatic optical resolution by stereoselective hydrolysis can be carried out by the customary methods familiar to those skilled in the art of enzymatic reactions. Homogeneous or heterogeneous systems can be used. Useful solvents or diluents include water, organic solvents, mixtures of two or more organic solvents or mixtures of water with one or more organic solvents. However, in view of the nature of the reaction at least as much water as is required for the desired hydrolysis of the ester to give the carboxylic acid must be present in the reaction mixture in addition to any organic solvents. Examples of suitable organic solvents include alcohols, for example ($C_1$–$C_4$)-alkanols such as methanol, ethanol, iso-propanol or tert-butanol, ethers, for example dialkyl ethers such as diisopropyl ether or tert-butyl methyl ether, ethylene glycol ethers and diethylene glycol ethers such as 1,2-dimethoxyethane or cyclic ethers such as tetrahydrofuran or dioxane, ketones, for example ($C_3$–$C_6$)-alkanones such as acetone or butanone, amides such as dimethylformamide or N-methylpyrrolidone, or saturated or aromatic hydrocarbons such as hexane, heptane, cyclohexane or toluene. The optical resolution of the invention is advantageously carried out in water or a mixture of water and one or more organic solvents, and more advantageously in a mixture of water and one or two organic cosolvents. The content of organic solvents in a mixture of water and organic solvents is preferably from about 5 to about 80% by volume, in particular from about 5 to about 30% by volume, for example from about 10 to about 20% by volume (percentages by volume determined from the volumes of the solvents employed). The amount of solvent or solvent mixture is generally chosen such that the reaction mixture comprises from about 1 to about 50% by weight of the starting compound of the formula I, preferably from about 5 to about 20% by weight.

Depending on the enzyme used and the compound of the formula I used, it can be advantageous to carry out the process of the invention in a certain pH range, for example at a pH in the range from about 5 to about 9, in particular in the range from about 6 to about 8, for example at a pH of about 7. To maintain the pH range, a suitable buffer can be added to the reaction medium or other measures can be taken. Examples of useful buffers include phosphate buffers or Tris buffers (=1,1,1-tris(hydroxymethyl)methylamine) buffer. The buffers can be used, for example, as approximately 0.01 molar to approximately 1 molar aqueous solutions which, optionally after addition of organic solvents, can serve as the reaction medium.

The process of the invention is preferably carried out with stirring of the reaction mixture at temperatures from about 10° C. to about 80° C., preferably from about 15° C. to about 60° C., for example from about 15° C. to about 40° C.

Useful enzymes for the optical resolution of the compounds of the formula I include in particular esterases and, since the reacting group in the compound of the formula I is a carboxylic ester group, specifically carboxylic acid esterases or carboxyl esterases, where however, as mentioned above, lipases are less suitable. Preferred esterases are those from mammalian livers, for example, porcine liver esterase (PLE; Sigma Chemical Co. or Roche Diagnostics), which can also be used in the form of isoenzyme fractions such as Chirazyme E-1 and Chirazyme E-2 (Roche Diagnostics), or rabbit liver esterase (Sigma Chemical Co.). The enzymes can also be used in the form of mixtures or in the form of customary mammalian liver acetone powders, for example liver acetone powder from the horse, calf, rat or rabbit (Sigma Chemical Co.). The enzymes can be used in free form, for example as a commercially available solid, solution or suspension, or immobilized form (see W. Hartmeier, Immobilized Biocatalysts, Springer Verlag Berlin, 1988). The enzyme quantity depends on the type and activity of enzyme used, the compound of the formula I used, the reaction conditions, the desired degree of conversion and the desired reaction time, and can be selected freely or, if desired, can easily be determined by simple preliminary experiments. By the appropriate choice of the parameters, for example, a reaction time of about a day can be set.

When the reaction has proceeded to the desired extent, unconverted ester, i.e. the remaining portion of the compound of the formula I wherein $R^3$ has a meaning other than hydrogen, and the acid formed, i.e. the compound of the formula I wherein $R^3$ is hydrogen, and thus the two enantiomeric forms of the compound of the formula I are separated from each other. To this end, the reaction mixture can be worked up by standard processes, for example by extraction or chromatographic methods. For example, the unconverted ester can be isolated by distribution of the reaction solution between water and a non-water-miscible organic solvent such as ethyl acetate, tert-butyl methyl ether or dichloromethane, and drying and concentration of the organic phase. The resulting acid can then be isolated by acidifying the aqueous phase obtained and extracting, for example, with ethyl acetate or dichloromethane, and drying and concentrating the organic phase. If appropriate, the products obtained can be further purified by customary processes. If required, the reaction mixture can be partially concentrated before the workup and/or a specific pH can be set, for example a pH in the basic range for extraction of the ester. The products can also be isolated in the form of salts. The recovery of the enzyme can take place by freeze-drying. The removal of the enzyme and its reuse in a later batch can be made easier by immobilization.

By conducting the reaction in an suitable manner it is always possible to obtain at least one of the two enantiomeric forms of the compound of the formula I in enantiomerically pure (optically pure) form or substantially enantiomerically pure (substantially optically pure) form. When the desired enantiomerically pure form occurs as the carboxylic acid wherein $R^3$ in the formula I is hydrogen, the enzymatic ester cleavage is expediently ended when less than 50% or at most 50% of the ester used in racemic form has been converted. When the desired enantiomerically pure form occurs as the ester wherein $R^3$ in the formula I has a meaning other than hydrogen, enzymatic ester-cleavage is expediently not ended until at least 50% or more than 50% of the ester used in racemic form has been converted. The determination of the conversion of an enzymatic reaction can, for example, take place simultaneously with the determination of the optical purities of the two reaction products, the acid occurring in one configuration and the ester occurring in the opposite configuration, by high pressure liquid chromatography (HPLC) using an optically active stationary phase. The enantiomeric purity (optical purity) of an obtained product can, for example, be given by the customary ee value (enantiomeric excess), which is the ratio of the difference of the quantities of both enantiomers to the sum of the quantities of both enantiomers. It is preferred to produce by the process of the invention at least one of the enantiomeric forms of the compound of the formula I in substantially enantiomerically pure form (substantially optically pure form) with an enantiomeric excess ee of at least about 90%, more preferably at least about 95%, most preferably at least about 98%. Products having an enantiomeric excess ee of at least about 98% are considered as enantiomerically pure (optically pure).

The resulting acid or remaining ester having the undesired configuration from the process of the invention can, if desired, be re-esterified by known methods and racemized and can then be reused in the enzymatic optical resolution, so that the yield of the desired enantiomer can be increased to over 50%. For example, non-racemic acids can be converted to the racemic mixture by conversion to the ester under basic conditions, for example, by warming with alcohol of the formula $R^3$ OH in the presence of the sodium alkoxide of the formula $R^3$ONa, and reused in the optical resolution.

When the desired enantiomer from the optical resolution of the invention occurs as a carboxylic acid, but an ester is required for the following step in the synthesis of the active ingredient, the acid can be converted to an ester by known esterification methods without racemization or inversion (see e.g. E. Haslam, Tetrahedron 1980, 36, 2409). Accordingly, when the desired enantiomer from the optical resolution of the invention occurs as an ester, but a carboxylic acid or other carboxylic acid derivative is required for the following step in the synthesis of the active ingredient, the ester can be converted by known methods without racemization or inversion to the carboxylic acid or a carboxylic acid derivative (see e.g. C. J. Salomon et al., Tetrahedron 1993, 49, 3691).

The present invention also provides a process for the kinetic optical resolution or enantiomer separation of a compound of the formula Ie,

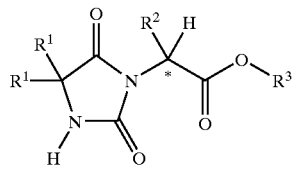

wherein
the two $R^1$ residues are identical and are hydrogen, fluorine, $(C_1-C_4)$-alkyl, $(C_2-C_4)$-alkenyl, $(C_2-C_4)$-alkynyl or $(C_3-C_4)$-cycloalkyl, where alkyl, alkenyl, alkynyl and cycloalkyl can be substituted by 1, 2 or 3 identical or different substituents selected from the group consisting of fluorine, chlorine, bromine and methoxy, or the two $R^1$ residues together are tetramethylene —$(CH_2)_4$— or pentamethylene —$(CH_2)_5$—;

$R^2$ is fluorine, chlorine, bromine, nitro, cyano, hydroxyl, methoxy, acetylamino, tert-butyloxycarbonylamino, benzyloxycarbonylamino, methylmercapto, tert-butylmercapto, $(C_1-C_{10})$-alkyl, aryl, aryl-$(C_1-C_{10})$-alkyl-, heteroaryl, heteroaryl-$(C_1-C_{10})$-alkyl-, $(C_2-C_{10})$-alkenyl, $(C_2-C_{10})$-alkynyl, $(C_3-C_7)$-cycloalkyl or $(C_3-C_7)$-cycloalkyl-$(C_1-C_{10})$-alkyl-, where alkyl, aryl, heteroaryl, alkenyl, alkynyl and cycloalkyl can be substituted by 1, 2 or 3 identical or different substituents selected from the group consisting of fluorine, chlorine, bromine, iodine, trifluoromethyl, methyl, nitro, cyano, acetylamino, 9-fluoroenylmethyloxycarbonylamino, tert-butyloxycarbonylamino, benzyloxycarbonylamino, mercapto, methylmercapto, tert-butylmercapto, hydroxyl, methoxy, ethoxy and COOR$^4$;

$R^3$ is $(C_1-C_{10})$-alkyl, aryl-$(C_1-C_{10})$-alkyl-, $(C_2-C_{10})$-alkenyl, $(C_3-C_{10})$-alkynyl, $(C_3-C_7)$-cycloalkyl or $(C_3-C_7)$-cycloalkyl-$(C_1-C_{10})$-alkyl-, where alkyl, aryl, alkenyl, alkynyl and cycloalkyl can be substituted by 1, 2 or 3 identical or different substituents selected from the group consisting of fluorine, chlorine, bromine, iodine, trifluoromethyl, methyl, cyano, nitro, acetylamino, tert-butyloxycarbonylamino, benzyloxycarbonylamino, hydroxyl, methoxy, ethoxy and COOR$^5$;

$R^4$ and $R^5$, which can be identical or different, are hydrogen, $(C_1-C_4)$-alkyl, $(C_2-C_4)$-alkenyl or aryl-$(C_1-C_{10})$-alkyl-;

or of a salt thereof, which comprises subjecting a mixture of the enantiomeric forms of the compound of the formula Ie to an enzymatic hydrolysis with the aid of an esterase and separating the converted and unconverted compounds from each other. All of the above explanations relating to the compounds of the formula I correspondingly apply to the compounds of the formula Ie and to the process for the kinetic optical resolution or enantiomer separation of these compounds, for example the preferred meanings of residues, the way of conducting the process, or the way of separating the unreacted compound of the formula Ie from the corresponding carboxylic acid formed wherein $R^3$ in the formula Ie is hydrogen or its salt.

The processes of the present invention allow the economical and fast production of substantially enantiomerically pure forms of the compounds of the formula I by technically simple measures. They require no equimolar quantities of optically pure starting materials or auxiliaries, no expensive reactants or solvents and no complex and cost-intensive process steps, and they substantially improve the overall process for synthesizing the corresponding active pharmaceutical ingredients.

The following examples illustrate the present invention.

EXAMPLES

The phosphate buffer used was a 0.1 M sodium potassium phosphate buffer of pH value 7.0, which was prepared from potassium dihydrogenphosphate and sodium hydroxide according to CRC Handbook of Chemistry and Physics, R. C. Weast (editor), 49. edition, 1968–1969, Cleveland (Ohio), page D-79.

The enzymes used are abbreviated as follows:
PLE porcine liver esterase (Technical Grade, Suspension; Roche Diagnostics)
RLE rabbit liver esterase (Sigma Chemical Co.)
CLAP calf liver acetone powder (Sigma Chemical Co.)
HLAP horse liver acetone powder (Sigma Chemical Co.)
RLAP rabbit liver acetone powder (Sigma Chemical Co.)

The optical purity of the esters and acids was determined by HPLC using a chiral phase with UV detection under the following conditions:
HPLC (method A): column Chiralpak AD 250×4.6 (Daicel); eluent n-hexane/isopropanol (25:1)+0.1% trifluoroacetic acid; flow 1 ml/min; temperature 30° C.; detection wavelength 202.6 nm.
HPLC (methode B): column Chiralpak AD 250×4.6 (Daicel); eluent n-hexane/isopropanol (25:1)+0.1% trifluoroacetic acid; flow 1 ml/min; temperature 30° C.; detection wavelength 205.4 nm.

The isolated products and crude product mixtures were identified by $^1$H-NMR spectra and/or mass spectra (MS) and/or by HPLC retention times.

Example 1

25 mg of methyl (RS)-2-(4,4-dimethyl-2,5-dioxoimidazolidin-1-yl)-4-methylpentanoate in 3 ml of phosphate buffer and 0.5 ml of acetone were mixed with 2 to 5 mg of Chirazyme E-1 (Roche Diagnostics) at 20 to 25° C. and the reaction mixture stirred at this temperature for 22 to 23 h. A sample was taken and analyzed by HPLC (method A). The optical purity ee of the unconverted S ester was >99%, the optical purity ee of the R acid formed was 58%.

Example 2

25 mg of ethyl (RS)-2-(4,4-dimethyl-2,5-dioxoimidazolidin-1-yl)-4-methylpentanoate in 3 ml of phosphate buffer and 0.5 ml of ethanol were mixed with 1 drop of PLE at 20 to 25° C. and the reaction mixture stirred at this temperature for 1 day. A sample was taken and analyzed by HPLC (method A). The optical purity ee of the unconverted S ester was 68%, the optical purity ee of the R acid formed was 93%.

Example 3

2.0 g of ethyl (RS)-2-(4,4-dimethyl-2,5-dioxoimidazolidin-1-yl)-4-methylpentanoate in 200 ml of phosphate buffer and 34 ml of ethanol were mixed with 10 drops of PLE at 20 to 25° C. and the reaction mixture stirred at this temperature until a conversion of about 36% was attained. The reaction mixture was extracted with ethyl acetate and the combined organic phases dried over magnesium sulfate. Concentration in vacuo gave 1.0 g of unconverted S ester having an optical purity of 64.8% ee (HPLC, method A). Analytical data of the unconverted S ester:

$^1$H-NMR (CDCl$_3$, 300 MHz):, δ=0.95 (d, J=7 Hz, 6H, CH(C$\underline{H}_3$)$_2$), 1.25 (t, J=7.5 Hz, 3H, OCH$_2$C$\underline{H}_3$), 1.46 (s, 6H, C(CH$_3$)$_2$), 1.5 (m, 1H, C$\underline{H}$(CH$_3$)$_2$), 1.88 (m, 1H, CHC$\underline{H}_2$CH), 2.30 (m, 1H, CHC$\underline{H}_2$CH), 4.20 (m, 2H, OC$\underline{H}_2$CH$_3$), 4.70 (dd, J$_1$=10 Hz, J$_2$=4 Hz, 1H, N—C$\underline{H}$—CH$_2$), 5.8 ppm (s, br, 1H, NH).

The aqueous phase obtained after extraction with ethyl acetate was acidified to pH 3 using dilute hydrochloric acid and extracted with ethyl acetate. The combined organic phases were dried over magnesium sulfate. Concentration in vacuo gave 0.65 9 of R acid having an optical purity of 94% ee (HPLC, method A). Analytical data of the R acid obtained:

$^1$H-NMR (CDCl$_3$, 300 MHz):, δ=0.9–1.0 (m, 6H, CH(C$\underline{H}_3$)$_2$), 1.46 (s, 6H, C(CH$_3$)$_2$), 1.5 (m, 1H, C$\underline{H}$(CH$_3$)$_2$), 1.88 (m, 1H, CHC$\underline{H}_2$CH), 2.30 (m, 1H, CHC$\underline{H}_2$CH), 4.75 (dd, J$_1$=10 Hz, J$_2$=4 Hz, 1H, N—C$\underline{H}$—CH$_2$), 6.75 (s, 1H, NH), 8.3 (s, br, 1H, COOH). MS (ESI): m/z=243 ([M+H]$^+$; 100%), 197 ([M-COOH]$^+$; 22%).

Example 4

25 mg of ethyl (RS)-2-(4,4-dimethyl-2,5-dioxoimidazolidin-1-yl)-4-methylpentanoate in 3 ml of phosphate buffer and 0.5 ml of acetone were mixed with 1 drop of PLE at 20 to 25° C. and the reaction mixture stirred at this temperature until a conversion of about 53% was attained. The reaction mixture was extracted with ethyl acetate and the organic phase analyzed by HPLC (method A). The optical purity ee of the unconverted S ester was >99%.

Example 5

25 mg of ethyl (RS)-2-(4,4-dimethyl-2,5-dioxoimidazolidin-1-yl)-4-methylpentanoate in 3 ml of phosphate buffer and 0.5 ml of n-heptane were mixed with 3 to 5 mg of HLAP at 20 to 25° C. and the reaction mixture stirred at this temperature. After a conversion of about 50%, a sample was taken and analyzed by HPLC (method A). The optical purity ee of unconverted S ester was 93%, the optical purity ee of the R acid formed was 94%.

Example 6

25 mg of ethyl (RS)-2-(4,4-dimethyl-2,5-dioxoimidazolidin-1-yl)-4-methylpentanoate in 3 ml of phosphate buffer and 0.5 ml of acetone were mixed with 3 to 5 mg of RLAP at 20 to 25° C. and the reaction mixture stirred at this temperature. After a conversion of about 52 to 55%, a sample was taken and analyzed by HPLC (method A). The optical purity ee of the unconverted S ester was >98%, the optical purity ee of the R acid formed was 80%.

Example 7

25 mg of ethyl (RS)-2-(4,4-dimethyl-2,5-dioxoimidazolidin-1-yl)-4-methylpentanoate in 3 ml of phosphate buffer and 0.5 ml of cyclohexane were mixed with 3 to 5 mg of HLAP at 20 to 25° C. and the reaction mixture stirred at this temperature. After a conversion of about 50%, a sample was taken and analyzed by HPLC (method A). The optical purity ee of the unconverted S ester was >99%, the optical purity ee of the R acid formed was >95%.

Example 8

25 mg of ethyl (RS)-2-(4,4-dimethyl-2,5-dioxoimidazolidin-1-yl)-4-methylpentanoate in 3 ml of phosphate buffer and 0.5 ml of n-heptane were mixed with 1 drop of PLE at 20 to 25° C. and the reaction mixture stirred at this temperature. After a conversion of about 54%, a sample was taken and analyzed by HPLC (method A). The optical purity ee of the unconverted S ester was 93%, the optical purity ee of the R acid formed was 79%.

Example 9

25 mg of ethyl (RS)-2-(4,4-dimethyl-2,5-dioxoimidazolidin-1-yl)-4-methylpentanoate in 3 ml of phosphate buffer and 0.5 ml of diisopropyl ether were mixed with 3 to 5 mg of HLAP at 20 to 25° C. and the reaction mixture stirred at this temperature. After a conversion of about 53%, a sample was taken and analyzed by HPLC (method A). The optical purity ee of the unconverted S ester was 98%, the optical purity ee of the R acid formed was >86%.

Example 10

25 mg of ethyl (RS)-2-(4,4-dimethyl-2,5-dioxoimidazolidin-1-yl)-3-cyclopropyl-propionate in 3 ml of phosphate buffer and 0.5 ml of cyclohexane were mixed with 3 to 5 mg of HLAP at 20 to 25° C. and the reaction mixture stirred at this temperature. After a conversion of about 37%, a sample was taken and analyzed by HPLC (method B). The optical purity ee of the unconverted S ester was 55%, the optical purity ee of the R acid formed was 94%.

Example 11

25 mg of ethyl (RS)-2-(4,4-dimethyl-2,5-dioxoimidazolidin-1-yl)-4-methylpentanoate in 3 ml of phosphate buffer and 0.5 ml of tert-butyl methyl ether were mixed with 3 to 5 mg of HLAP at 20 to 25° C. and the reaction mixture stirred at this temperature. After a conversion of about 47%, a sample was taken and analyzed by HPLC (method A). The optical purity ee of the unconverted S ester was 83%, the optical purity ee of the R acid formed was >92%.

Example 12

25 mg of ethyl (RS)-2-(4,4-dimethyl-2,5-dioxoimidazolidin-1-yl)-4-methylpentanoate in 3 ml of phosphate buffer and 0.5 ml of 1,2-dimethoxyethane were mixed with 1 drop of PLE at 20 to 25° C. and the reaction mixture stirred at this temperature for 1 day. The reaction mixture was extracted with ethyl acetate and the organic phase analyzed by HPLC (method A). The optical purity ee of the unconverted S ester was 99%.

Example 13

25 mg of ethyl (RS)-2-(4,4-dimethyl-2,5-dioxoimidazolidin-1-yl)-4-methylpentanoate in 3 ml of phosphate buffer and 0.5 ml of acetone were mixed with 1 drop of RLE at 20 to 25° C. and the reaction mixture stirred at this temperature for 21 h. A sample was taken and analyzed by HPLC (method A). The optical purity ee of the unconverted S ester was 98%, the optical purity ee of the R acid formed was 79%.

Example 14

25 mg of ethyl (RS)-2-(4,4-dimethyl-2,5-dioxoimidazolidin-1-yl)-4-methylpentanoate in 3 ml of phosphate buffer and 0.5 ml of tert-butyl methyl ether were mixed with 3 to 5 mg of RLAP at 20 to 25° C. and the reaction mixture stirred at this temperature. After a conversion of about 49%, a sample was taken and analyzed by HPLC (method A). The optical purity ee of the unconverted S ester was 89%, the optical purity ee of the R acid formed was 93%.

Example 15

25 mg of methyl (RS)-2-(4,4-dimethyl-2,5-dioxoimidazolidin-1-yl)-4-methylpentanoate in 3 ml of phosphate buffer and 0.5 ml of acetone were mixed with 3 to 5 mg of RLAP at 20 to 25° C. and the reaction mixture stirred at this temperature for 22 to 23 h. A sample was taken and analyzed by HPLC (method A). The optical purity ee of the unconverted S ester was >99%, the optical purity ee of R acid formed was 54%.

Example 16

25 mg of ethyl (RS)-2-(4,4-dimethyl-2,5-dioxoimidazolidin-1-yl)-4-methylpentanoate in 3 ml of phosphate buffer and 0.5 ml of acetone were mixed with 3 to 5 mg of Chirazyme E-1 (Roche Diagnostics) at 20 to 25° C. and the reaction mixture stirred at this temperature. After a conversion of about 45%, a sample was taken and analyzed by HPLC (method A). The optical purity ee of the unconverted S ester was 77%.

Example 17

25 mg of ethyl (RS)-2-(4,4-dimethyl-2,5-dioxoimidazolidin-1-yl)-4-methylpentanoate in 3 ml of phosphate buffer and 0.5 ml of dimethylformamide were mixed with 1 drop of PLE at 20 to 25° C. and the reaction mixture stirred at this temperature for 1 day. A sample was taken and analyzed by HPLC (method A). The optical purity ee of the unconverted S ester was 97%, the optical purity ee of the R acid formed was 75%.

Example 18

25 mg of ethyl (RS)-2-(4,4-dimethyl-2,5-dioxoimidazolidin-1-yl)-4-methylpentanoate in 3 ml of phosphate buffer and 0.5 ml of acetone were mixed with 3 to 5 mg of Chirazyme E-2 (Roche Diagnostics) at 20 to 25° C. and the reaction mixture stirred at this temperature. After a conversion of about 50%, a sample was taken and analyzed by HPLC (method A). The optical purity ee of the unconverted S ester was 95%.

Example 19

25 mg of methyl (RS)-2-(4,4-dimethyl-2,5-dioxoimidazolidin-1-yl)-4-methylpentanoate in 3 ml of phosphate buffer and 0.5 ml of acetone were mixed with 1 drop of PLE at 20 to 25° C. and the reaction mixture stirred at this temperature for 22 to 23 h. A sample was taken and analyzed by HPLC (method A). The optical purity ee of the unconverted S ester was >99%, the optical purity ee of the R acid formed was 57.6%.

Example 20

25 mg of methyl (RS)-2-(4,4-dimethyl-2,5-dioxoimidazolidin-1-yl)-4-methylpentanoate in 3 ml of phosphate buffer and 0.5 ml of acetone were mixed with 2 to 5 mg of Chirazyme E-2 (Roche Diagnostics) at 20 to 25° C. and the reaction mixture stirred at this temperature for 22 to 23 h. A sample was taken and analyzed by HPLC (method A). The optical purity ee of the unconverted S ester was 97.7%, the optical purity ee of the R acid formed was 58%.

Example 21

25 mg of ethyl (RS)-2-(4,4-dimethyl-2,5-dioxoimidazolidin-1-yl)-4-methylpentanoate in 3 ml of phosphate buffer and 0.5 ml of tert-butyl methyl ether were mixed with 3 to 5 mg of CLAP at 20 to 25° C. and the reaction mixture stirred at this temperature. After a conversion of about 33%, a sample was taken and analyzed by HPLC (method A).

The optical purity ee of unconverted S ester was 46%, the optical purity ee of the R acid formed was 92%.

Example 22

25 mg of ethyl (RS)-2-(4,4-dimethyl-2,5-dioxoimidazolidin-1-yl)-4-methylpentanoate in 3 ml of phosphate buffer and 0.5 ml of diisopropyl ether were mixed with 1 drop of PLE at 20 to 25° C. and the reaction mixture stirred at this temperature for 1 day. The reaction mixture was extracted with ethyl acetate and the organic phase analyzed by HPLC (method A). The optical purity ee of the unconverted S ester was 96.7%.

Example 23

25 mg of ethyl (RS)-2-(4,4-dimethyl-2,5-dioxoimidazolidin-1-yl)-3-cyclopropyl-propionate in 3 ml of phosphate buffer and 0.5 ml of ethanol were mixed with 1 drop of PLE at 20 to 25° C. and the reaction mixture stirred at this temperature. After a conversion of about 19%, a sample was taken and analyzed by HPLC (method B). The optical purity ee of unconverted S ester was 23%, the optical purity ee of the R acid formed was >99%.

What is claimed is:

1. A process for the preparation of a compound of the formula I,

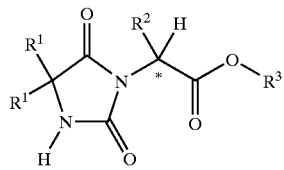

wherein
the two $R^1$ residues are identical and are hydrogen, fluorine, $(C_1-C_4)$-alkyl, $(C_2-C_4)$-alkenyl, $(C_2-C_4)$-alkynyl or $(C_3-C_4)$-cycloalkyl, where alkyl, alkenyl, alkynyl and cycloalkyl can be substituted by 1, 2 or 3 identical or different substituents selected from the group consisting of fluorine, chlorine, bromine and methoxy, or the two $R^1$ residues together are tetramethylene —$(CH_2)_4$— or pentamethylene —$(CH_2)_5$—;
$R^2$ is fluorine, chlorine, bromine, nitro, cyano, hydroxyl, methoxy, acetylamino, tert-butyloxycarbonylamino, benzyloxycarbonylamino, methylmercapto, tert-butylmercapto, $(C_1-C_{10})$-alkyl, aryl, aryl-$(C_1-C_{10})$-alkyl-, heteroaryl, heteroaryl-$(C_1-C_{10})$-alkyl-, $(C_2-C_{10})$-alkenyl, $(C_2-C_{10})$-alkynyl, $(C_3-C_7)$-cycloalkyl or $(C_3-C_7)$-cycloalkyl-$(C_1-C_{10})$-alkyl-, where alkyl, aryl, heteroaryl, alkenyl, alkynyl and cycloalkyl can be substituted by 1, 2 or 3 identical or different substituents selected from the group consisting of fluorine, chlorine, bromine, iodine, trifluoromethyl, methyl, nitro, cyano, acetylamino, 9-fluoroenylmethyloxycarbonylamino, tert-butyloxycarbonylamino, benzyloxycarbonylamino, mercapto, methylmercapto, tert-butylmercapto, hydroxyl, methoxy, ethoxy and $COOR^4$;
$R^3$ is hydrogen, $(C_1-C_{10})$-alkyl, aryl-$(C_1-C_{10})$-alkyl-, $(C_2-C_{10})$-alkenyl, $(C_3-C_{10})$-alkynyl, $(C_3-C_7)$-cycloalkyl or $(C_3-C_7)$-cycloalkyl-$(C_1-C_{10})$-alkyl-, where alkyl, aryl, alkenyl, alkynyl and cycloalkyl can be substituted by 1, 2 or 3 identical or different substituents selected from the group consisting of fluorine, chlorine, bromine, iodine, trifluoromethyl, methyl, cyano, nitro, acetylamino, tert-butyloxycarbonylamino, benzyloxycarbonylamino, hydroxyl, methoxy, ethoxy and $COOR^5$;
$R^4$ and $R^5$, which can be identical or different, are hydrogen, $(C_1-C_4)$-alkyl, $(C_2-C_4)$-alkenyl or aryl-$(C_1-C_{10})$-alkyl-;

or of a salt thereof, in substantially enantiomerically pure form, which process comprises subjecting a mixture of the enantiomeric forms of a compound of the formula I wherein $R^3$ has a meaning other than hydrogen, to an enzymatic hydrolysis with the aid of an esterase and separating the converted and unconverted compounds from each other.

2. The process as claimed in claim 1, wherein the two $R^1$ residues in the formula I are identical and are hydrogen, methyl, ethyl, propyl or trifluoromethyl, or both $R^1$ residues together are tetramethylene or pentamethylene.

3. The process as claimed in claim 1, wherein $R^2$ in the formula I is $(C_1-C_6)$-alkyl, phenyl, phenyl-$(C_1-C_4)$-alkyl-, $(C_3-C_6)$-cycloalkyl or $(C_3-C_6)$-cycloalkyl-$(C_1-C_4)$-alkyl-, where alkyl, cycloalkyl and phenyl can be substituted as described in claim 1.

4. The process as claimed in claim 1, wherein the two $R^1$ residues in the formula I are identical and are hydrogen, methyl or trifluoromethyl, or the two $R^1$ residues together are tetramethylene or pentamethylene;
$R^2$ is $(C_1-C_6)$-alkyl or $(C_3-C_6)$-cycloalkyl-$(C_1-C_2)$-alkyl-; and
$R^3$ is hydrogen or $(C_1-C_4)$-alkyl.

5. The process as claimed in claim 1, wherein the enzyme used is mammalian liver esterase or mammalian liver acetone powder.

6. The process as claimed in claim 1, wherein the reaction is carried out in a mixture of water and one or more organic solvents.

7. The process as claimed in claim 1, wherein the reaction is carried out in the pH range from 5 to 9.

8. A process for the kinetic optical resolution of a compound of the formula Ie,

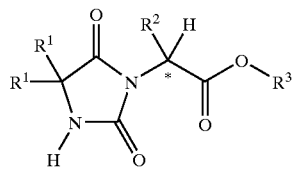

wherein
the two $R^1$ residues are identical and are hydrogen, fluorine, $(C_1-C_4)$-alkyl, $(C_2C_4)$-alkenyl, $(C_2-C_4)$-alkynyl or $(C_3-C_4)$-cycloalkyl, where alkyl, alkenyl, alkynyl and cycloalkyl can be substituted by 1, 2 or 3 identical or different substituents selected from the group consisting of fluorine, chlorine, bromine and methoxy, or the two $R^1$ residues together are tetramethylene —$(CH_2)_4$— or pentamethylene —$(CH_2)_5$—;
$R^2$ is fluorine, chlorine, bromine, nitro, cyano, hydroxyl, methoxy, acetylamino, tert-butyloxycarbonylamino, benzyloxycarbonylamino, methylmercapto, tert-butylmercapto, $(C_1-C_{10})$-alkyl, aryl, aryl-$(C_1-C_{10})$-alkyl-, heteroaryl, heteroaryl-$(C_1-C_{10})$-alkyl-, $(C_2-C_{10})$-alkenyl, $(C_2-C_{10})$-alkynyl, $(C_3-C_7)$-cycloalkyl or $(C_3-C_7)$-cycloalkyl-$(C_1-C_{10})$-alkyl-, where alkyl, aryl, heteroaryl, alkenyl, alkynyl and cycloalkyl can be substituted by 1, 2 or 3 identical or different substituents selected from the group consisting of fluorine, chlorine, bromine, iodine, trifluoromethyl, methyl, nitro, cyano, acetylamino, 9-fluoroenylmethyloxycarbonylamino, tert-butyloxycarbonylamino, benzyloxycarbonylamino, mercapto, methylmercapto, tert-butylmercapto, hydroxyl, methoxy, ethoxy and $COOR^4$;

$R^3$ is $(C_1-C_{10})$-alkyl, aryl-$(C_1-C_{10})$-alkyl-, $(C_2-C_{10})$-alkenyl, $(C_3-C_{10})$-alkynyl, $(C_3-C_7)$-cycloalkyl or $(C_3-C_7)$-cycloalkyl-$(C_1-C_{10})$-alkyl-, where alkyl, aryl, alkenyl, alkynyl and cycloalkyl can be substituted by 1, 2 or 3 identical or different substituents selected from the group consisting of fluorine, chlorine, bromine, iodine, trifluoromethyl, methyl, cyano, nitro, acetylamino, tert-butyloxycarbonylamino, benzyloxycarbonylamino, hydroxyl, methoxy, ethoxy and $COOR^5$;

$R^4$ and $R^5$, which can be identical or different, are hydrogen, $(C_1-C_4)$-alkyl, $(C_2-C_4)$-alkenyl or aryl-$(C_1-C_{10})$-alkyl-;

or of a salt thereof, which process comprises subjecting a mixture of the enantiomeric forms of the compound of the formula Ie to an enzymatic hydrolysis with the aid of an esterase and separating the converted and unconverted compounds from each other.

* * * * *